United States Patent
Akella et al.

(10) Patent No.: US 7,232,802 B2
(45) Date of Patent: Jun. 19, 2007

(54) COMPOSITIONS AND METHODS FOR PROMOTING MYOCARDIAL AND PERIPHERAL ANGIOGENESIS

(75) Inventors: Rama Akella, Austin, TX (US); John Ranieri, Atlanta, GA (US)

(73) Assignee: Zimmer Orthobiologics, Inc., Austin, TX (US)

( * ) Notice: Subject to any disclaimer, the term of this patent is extended or adjusted under 35 U.S.C. 154(b) by 53 days.

(21) Appl. No.: 10/027,015

(22) Filed: Dec. 21, 2001

(65) Prior Publication Data

US 2005/0143312 A1   Jun. 30, 2005

(51) Int. Cl.
*A61K 38/04* (2006.01)
*C07K 7/00* (2006.01)

(52) U.S. Cl. ............................ 514/17; 514/9; 530/329; 530/317; 435/7.1; 424/9.1

(58) Field of Classification Search ................. 514/17, 514/9; 530/329, 317; 435/7.1; 424/9.1
See application file for complete search history.

(56) References Cited

U.S. PATENT DOCUMENTS

| | | | |
|---|---|---|---|
| 4,699,788 A | 10/1987 | Catsimpoolas et al. | 424/104 |
| 4,895,838 A | 1/1990 | McCluer et al. | 514/54 |
| 4,900,673 A | 2/1990 | Harper et al. | 435/199 |
| 4,950,483 A | 8/1990 | Ksander et al. | 424/422 |
| 5,116,738 A | 5/1992 | Wang et al. | 435/69.1 |
| 5,141,905 A | 8/1992 | Rosen et al. | 435/69.1 |
| 5,187,076 A | 2/1993 | Wozney et al. | 435/69.1 |
| 5,219,576 A | 6/1993 | Chu et al. | 424/484 |
| 5,318,957 A | 6/1994 | Cid et al. | 514/8 |
| 5,328,695 A | 7/1994 | Lucas et al. | 424/426 |
| 5,371,191 A | 12/1994 | Poser et al. | 530/350 |
| 5,459,047 A | 10/1995 | Wozney et al. | 435/69.1 |
| 5,470,831 A | 11/1995 | Whitman et al. | 514/16 |
| 5,543,392 A | 8/1996 | Tomita et al. | 514/8 |
| 5,543,394 A | 8/1996 | Wozney et al. | 514/12 |
| 5,595,722 A | 1/1997 | Grainger et al. | 424/9.2 |
| 5,616,490 A | 4/1997 | Sullivan et al. | 435/366 |
| 5,631,142 A | 5/1997 | Wang et al. | 435/69.1 |
| 5,635,372 A | 6/1997 | Celeste et al. | 435/69.1 |
| 5,637,480 A | 6/1997 | Celeste et al. | 435/69.4 |
| 5,656,587 A | 8/1997 | Sporn et al. | 514/2 |
| 5,661,007 A | 8/1997 | Wozney et al. | 435/69.4 |
| 5,677,276 A | 10/1997 | Dickerson et al. | 514/8 |
| 5,703,043 A | 12/1997 | Celeste et al. | 514/12 |
| 5,705,477 A | 1/1998 | Sporn et al. | 514/2 |
| 5,846,770 A | 12/1998 | LaVallie et al. | 435/69.1 |
| 5,849,880 A | 12/1998 | Wozney et al. | 530/399 |
| 5,854,207 A | 12/1998 | Lee et al. | 514/2 |
| 5,866,364 A | 2/1999 | Israel et al. | 435/69.1 |
| 5,928,940 A | 7/1999 | Sampath et al. | 435/325 |
| 5,932,216 A | 8/1999 | Celeste et al. | 424/158.1 |
| 5,965,403 A | 10/1999 | Celeste et al. | 435/69.4 |
| 5,972,884 A | 10/1999 | Cohen et al. | 514/12 |
| 5,981,489 A | 11/1999 | Stevenson et al. | 514/15 |
| 5,994,094 A | 11/1999 | Hötten et al. | 435/69.1 |
| 6,051,648 A | 4/2000 | Rhee et al. | 525/54.1 |
| 6,120,760 A | 9/2000 | Hötten et al. | 424/85.1 |
| 6,124,273 A | 9/2000 | Drohan et al. | 514/55 |
| 6,150,328 A | 11/2000 | Wang et al. | 514/12 |
| 6,177,406 B1 | 1/2001 | Wang et al. | 514/12 |
| 6,197,550 B1 | 3/2001 | Hötten et al. | 435/69.5 |
| 6,211,157 B1 | 4/2001 | Benedict et al. | 514/21 |
| 6,468,960 B1 | 10/2002 | Lukanidin et al. | 514/2 |
| 6,498,142 B1 | 12/2002 | Sampath et al. | 514/12 |
| 2002/0025340 A1 | 2/2002 | Dyer | 424/486 |
| 2002/0040004 A1 | 4/2002 | Benedict et al. | 514/21 |
| 2003/0022828 A1 | 1/2003 | Akella et al. | 514/12 |
| 2003/0104977 A1 | 6/2003 | Ripamonti et al. | 514/2 |

FOREIGN PATENT DOCUMENTS

| | | |
|---|---|---|
| EP | 0433225 B1 | 6/1991 |
| EP | 0516901 A1 | 12/1992 |
| EP | 0747066 B1 | 12/1996 |
| WO | WO 97/41880 | 11/1997 |
| WO | WO 99/02674 | 1/1999 |
| WO | WO 99/31136 | 6/1999 |
| WO | WO 99/57146 | 11/1999 |
| WO | WO00/55206 | 9/2000 |
| WO | WO 02/00244 | 1/2002 |
| WO | WO 02/47713 | 6/2002 |
| WO | WO 03/060076 | 7/2003 |

OTHER PUBLICATIONS

Carron et al., *Cancer Research* 58:1930-1935 (May 1998).
Shpiro et al., *Mol. BioSyst.* 1:318-320 (Aug. 26, 2005).
Cuevas et al., "Fibroblast Growth Factor Protects the Kidney Against Ischemia-Reperfusion Injury," *Eur. J. Med. Res.*, 4:403-10, 1999.
Folkman, "Angiogenic Therapy of the Human Heart," *Circulation*, 97:628-29, 1998.
Freed et al., "Neocartilage formation in vitro and in vivo using cells cultured on synthetic biodegradable polymers," *J. Biomed. Mater. Res.*, 27:11-23, 1993.
Freedman and Isner, "Therapeutic Angiogenesis for Ischemic Cardiovascular Disease," *Molecular and Cellular Cardiology*, 33;379-93, 2001.

(Continued)

*Primary Examiner*—Chih-Min Kam
(74) *Attorney, Agent, or Firm*—Williams, Morgan & Amerson, P.C.

(57) ABSTRACT

Methods, compositions and devices are disclosed for use in growing new blood vessels to restore or improve blood flow to ischemic tissues and organs of the body. Compositions comprising IGD peptides, particularly GGIGDGG, are able to induce migration in human endothelial cells and promote vessel formation in an in vitro model assay system.

23 Claims, 6 Drawing Sheets

OTHER PUBLICATIONS

Hammerman, "Growth Factors in Renal Development," *Seminars in Nephrology*, 15:291-99, 1995.

Hirschberg et al., "Multicenter clinical trial of recombinant human insulin-like growth factor I in patients with acute renal failure," *Kidney International*, 55:2423-32, 1999.

Kawa-uchi et al., "Fibroblast growth factor enhances expression of TGFβ-stimulated-clone-22 gene in osteoblast-like cells," *Endocrine*, 3:833-37, 1995.

Laham et al., "Intrapericardial Delivery of Fibroblast Growth Factor-2 Induces Neovascularization in a Porcine Model of Chronic Myocardial Ischemia," *J. Pharmacol. Exp. Ther.*, 292:795-802, 2000.

Mueller et al., "Myocardial angiogenesis induction with bone protein derived growth factors (animal experiment)," *Swiss Med. Wkly*, 131:23-25, 2001.

Nakaoka et al., "Inhibition of Rat Vascular Smooth Muscle Proliferation In Vitro and In Vivo by Bone Morphogenetic Protein-2," *J. Clin. Invest.*, 100:2824-32, 1997.

Nishida et al., "Adenovirus-Mediated Gene Transfer to Nucleus Pulposus Cells," *Spine*, 23:2437-42, 1998.

Parsons-Wingerter et al., "A novel assay of angiogenesis in the quail chorioallantoic membrane: stimulation by bFGF and inhibition by angiostatin according to fractal dimension and grid intersection," *Microvasc. Res.*, 55:201-14, 1998.

Prochazka et al., "Epidermal Growth Factor and Insulin Growth Factor I Increase FSH-Stimulated Expansion of Porcine Cumulus Cells in Serum-free Medium," *J. Reproduction and Fertility*, 25:64, 2000.

Ramoshebi and Ripamonti, "Osteogenic protein-1, a bone morphogenetic protein, induces angiogenesis in the chick chorioallantoic membrane and synergizes with basic fibroblast growth factor and transforming growth factor-beta 1," *Anat. Rec.*, 259:97-107, 2000.

Sakaguchi et al., "A Combination of EGF and IGF-1 Accelerates the Progression of Meiosis in Bovine Follicular Oocytes In Vitro and Fetal Calf Serum Neutralizes the Acceleration Effect," *Theriogenology*, 54:1327-42, 2000.

Schumacher et al., "Induction of Neoangiogenesis in Ischemic Myocardium by Human Growth Factors," *Circulation*, 97:645-50, 1998.

Stelnicki et al., "Bone Morphogenetic Protein-2 Induces Scar Formation and Skin Maturation in the Second Trimester Fetus," *Plastic and Reconstructive Surgery*, 101:12-19, 1998.

Vukicevic et al., "Osteogenic Protein-1 (Bone Morphogenetic Protein-7) Reduces Severity of Injury After Ischemic Acute Renal Failure in Rat," *J. Clin. Invest.*, 102:202-14, 1998.

Wiley and Cunningham, "Epidermal Growth Factor Stimulates Fluid Phase Endocytosis in Human Fibroblasts Through a Signal Generated at the Cell Surface," *J. Cellular Biochem.*, 19:383-94, 1982.

Yamamoto et al., "Histologic evidence that basic fibroblast growth factor enhances the angiogenic effects of transmyocardial laser revascularization," *Basic Res. Cardiol.*, 95:55-63, 2000.

Yamashita et al., "Growth/Differentiation Factor-5 Induces Angiogenesis In Vivo," *Exper. Cell Res.*, 235:218-26, 1997.

Yonggang et al., "Percutaneous injection of bone morphogenetic protein and polyvinyl pyrrolidone composite," *J. Xi'an Medical University*, 22:132-33, 2001.

PCT Search Report from PCT/US02/41484, dated Aug. 12, 2004.

Chernousov et al., "Role of the I-9 and III-1 Modules of Fibronectin in Formation of an Extracellular Fibronectin Matrix," *J. Biol. Chem.*, 266:10851-58, 1991.

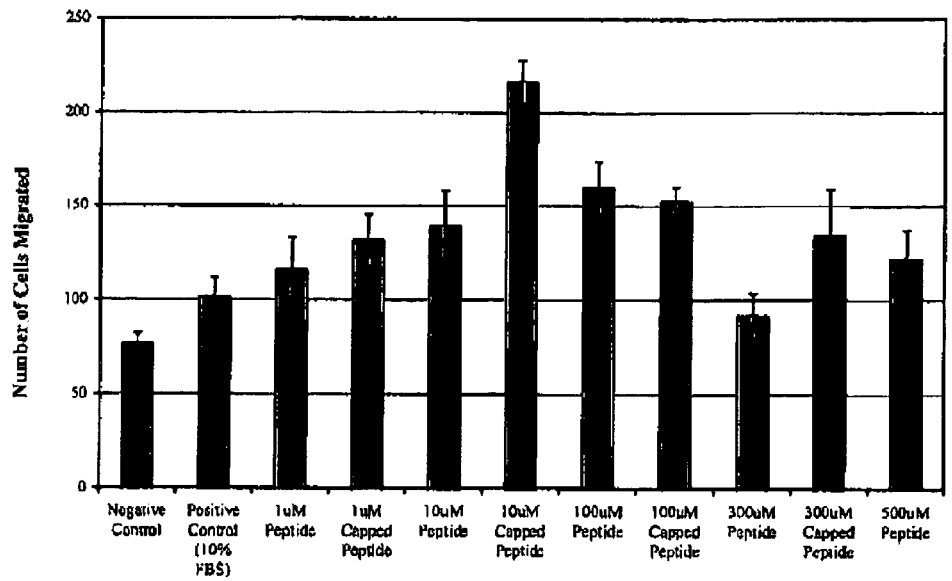

Figure 1A: Migration of Human aortic endothelial cells in response to IGD tripeptide, capped IGD tripeptide. A dose dependent effect was observed with the optimal concentration being 100 μM for the uncapped peptide. However, with the capped peptide better migration compared to the uncapped peptide was observed at a 10-fold lower concentration. The respective scramble peptides showed fewer number of cells migrating (data not shown)

Figure 1B: Migration of human aortic smooth muscle cells in response to the tripeptide
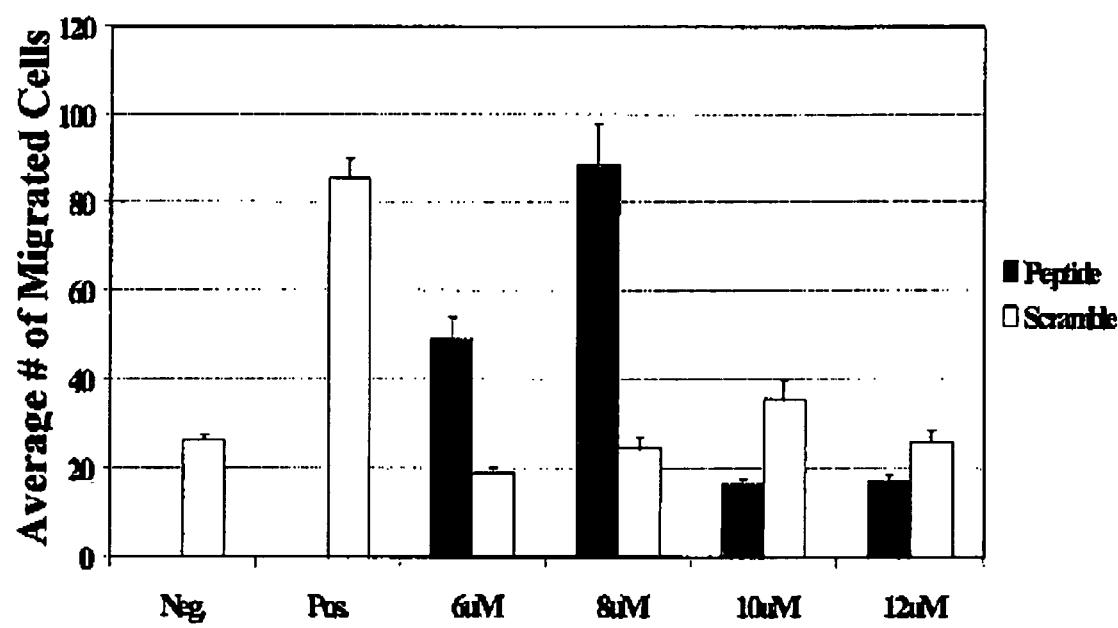

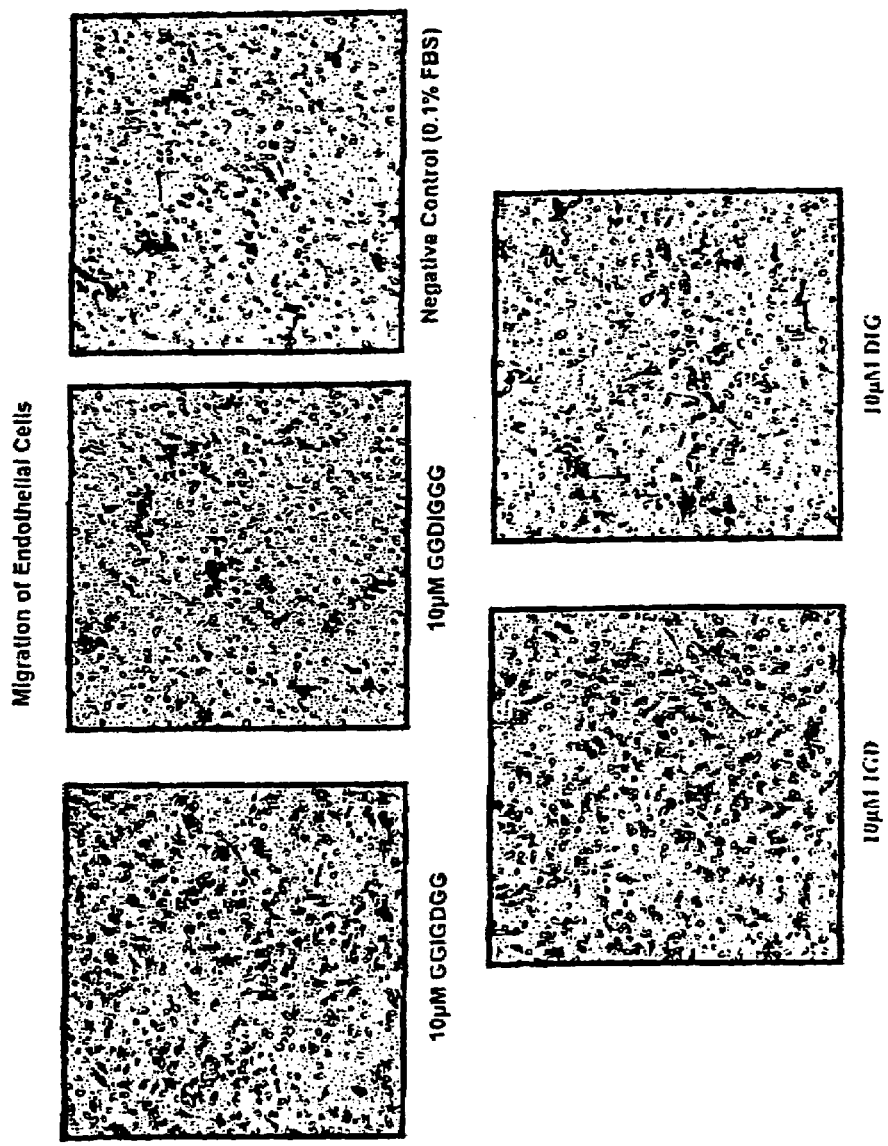
Figure 1C: This figure shows the migration of endothelial cells in a modified Boyden chamber assay in response to various treatment.

Proliferation of Human aortic endothelial cells in response to treatment with IGD tripeptide, the capped IGD tripeptide, and capped and uncapped scramble tripeptide, at two different concentrations.

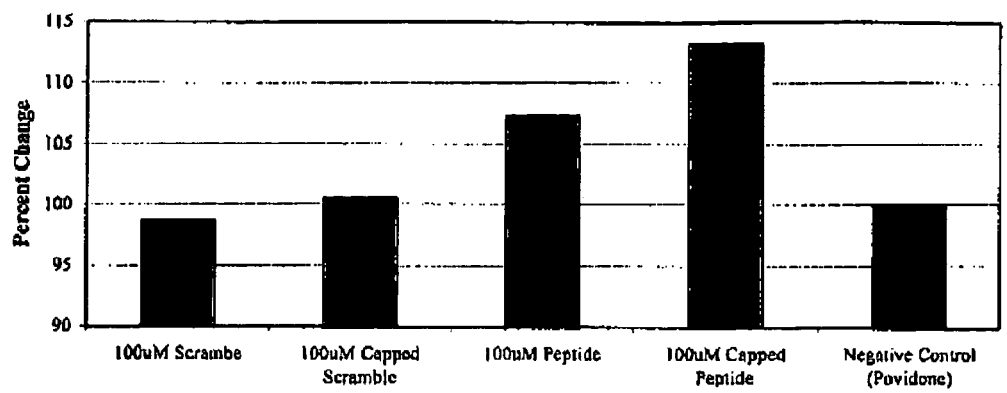
Figure 3A: Quail CAM assay showing increase in blood vessels in response to the peptide and the capped peptide compared to the respective scramble peptides. Data presented here is as a percent change over negative control, the negative being set at 100%. It can be seen that the capped peptide was better that the uncapped peptide at equivalent concentrations.

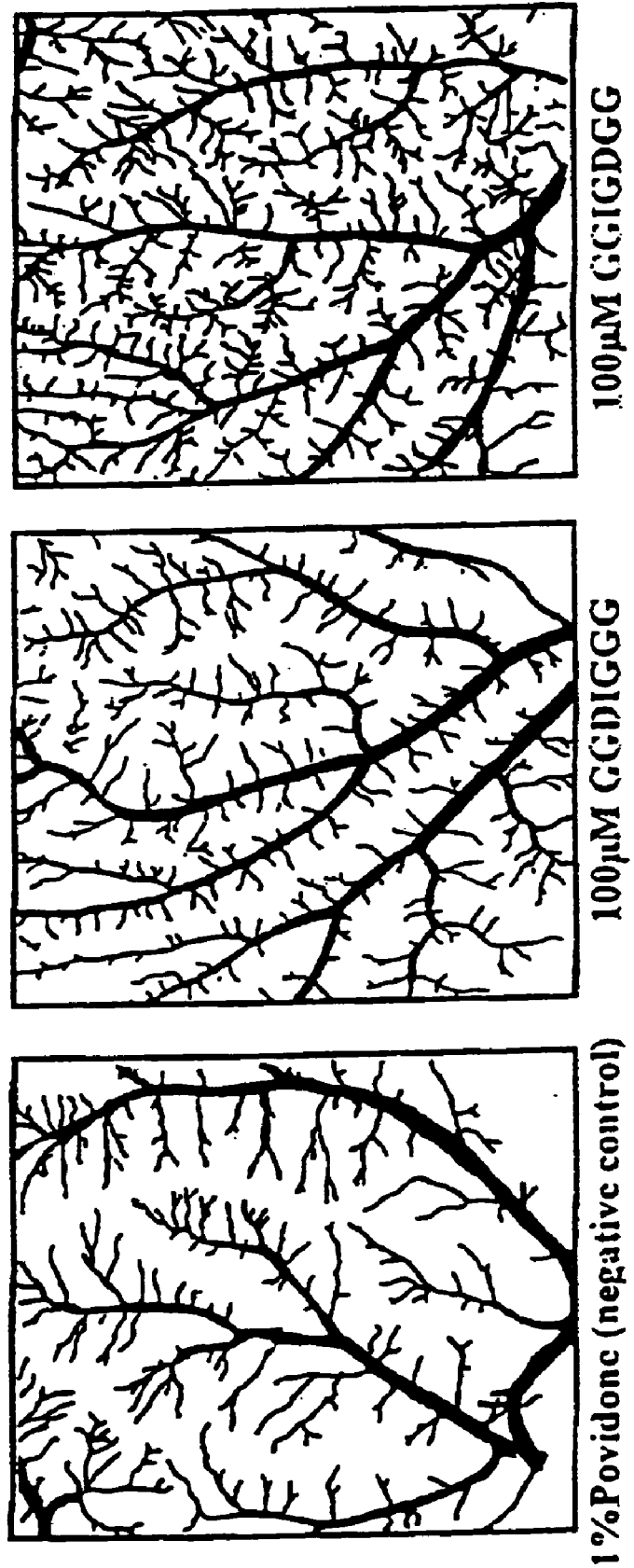
Figure 3B: Angiogenic response of the capped IGD-motif in the quail CAM assay.

COMPOSITIONS AND METHODS FOR PROMOTING MYOCARDIAL AND PERIPHERAL ANGIOGENESIS

BACKGROUND OF THE INVENTION

1. Field of the Invention

The present invention generally relates to the treatment of ischemic conditions of major organs in the human body by promoting growth of collateral vessels to increase blood flow to the target organs and tissues. More specifically, the invention relates to peptide based angiogenic compositions, methods and devices for treating cardiovascular disease associated with reduced blood flow arising from narrowing of a native blood vessel or occlusion of a bypass graft.

2. Description of Related Art

In the United States, cardiac failure due to underlying coronary heart disease is currently one of the leading causes of death. At the present time, coronary artery bypass graft (CABG) surgery and percutaneous transluminal coronary angioplasty (PTCA) are the most widely used interventions for treating advanced cardiac disease. In CABG, an autologous vessel is used to bypass the area of coronary obstruction or occlusion and to restore the blood flow. In PTCA, a catheter device is employed to unblock the clogged blood vessel to restore adequate blood flow to the heart and a metal stent is usually implanted to maintain vessel patency. Both of those procedures are considered to be highly invasive, are associated with a certain incidence of restenosis, and may not be appropriate for every patient in need of relief from coronary vessel obstructions-particularly when the patient is elderly or has undergone a previous CABG or PTCA procedure. Moreover, in peripheral vascular disease, when the vessels that supply blood to the legs, intestines and other areas of the body experience atherosclerotic narrowing, neither procedure may be an option because of the small size of the occluded peripheral vessels.

In some individuals, blood vessel occlusion is partially compensated by the spontaneous process of angiogenesis, or new vessel growth, in which new collateral vessels form over a period of time to provide natural bypasses around the occluded vessels. The process of angiogenesis generally involves basement membrane degradation and endothelial cell migration and proliferation to form capillaries which may develop further into mature vessels. Naturally occurring mitogenic factors released from lymphoid and endothelial cells can induce angiogenesis and promote neovascularization of damaged or blood starved tissue. The newly formed vessels can oftentimes supplement or entirely replace the function of the impaired vessels, thereby restoring blood flow to the deprived tissue served by the occluded vessels.

Some individuals are unable to generate sufficient collateral vessels to adequately compensate for diminished blood flow to the ischemic tissue. Therefore, a third treatment approach, still in development, endeavors to induce or enhance the growth of new blood vessels around an area of obstruction to restore adequate blood flow to the heart or other blood deprived tissue. Induced or promoted angiogenesis is believed by many investigators to offer the least invasive way to treat coronary heart disease, to be suitable for use in a large percentage of the patient population (including in particular some patients who are not candidates for either CABG or PTCA), and applicable for neovascularization of both myocardial and peripheral tissues.

Several angiogenic agents have recently been identified that promote angiogenesis through either direct attraction and/or induction of proliferation of endothelial cells, or indirect action by stimulating other cell types (e.g., mast cells or macrophages) that, in turn, produce angiogenic factors. Examples of these agents include vascular endothelial growth factor (VEGF), osteonectin or SPARC, basic fibroblast growth factor (bFGF), angiogenin, endothelial growth factor (EGF), platelet derived growth factor (PDGF), transforming growth factor-alpha (TGF-α), transforming growth factor-beta (TGF-β), and tumor necrosis factor-alpha (TNF-α). Each of these angiogenic agents or factors are either synthetic, meaning that they are manufactured chemically from non-living sources, or are produced by recombinant manufacturing processes (Freedman, S. B., and Isner, J. M., Therapeutic angiogenesis for ischemic cardiovascular disease, J. Mol. Cell Cardiol 33(3): 379–393 (2001)).

Another angiogenic agent, disclosed in co-assigned U.S. Pat. No. 6,211,157 (Benedict et al./Sulzer Biologics, Inc.), is a bone-derived angiogenic protein (BDAP) mixture that provides a more robust angiogenic response than many single factors such as bFGF or VEGF.

Many approaches to enhancement of localized angiogenesis and/or wound healing involve introduction of an extracellular matrix-like material that can serve as a support or scaffold at the desired site and with which the target cells may interact, usually via specific cell surface receptors, to promote cell proliferation. Extracellular matrix ("ECM") is the structurally stable material beneath the epithelia surrounding the cells of the connective tissue and constitutes a sort of natural scaffolding material. ECM can also be defined as the macromolecular components of connective tissue, generally consisting of proteoglycans, polysaccharides and proteins, which have major roles in cell shape, cell migration and differentiation, and control of cell growth. A subset of the ECM family of proteins is the adhesion proteins. The two major adhesion proteins, fibronectin and laminin, are involved in many cellular processes, including tissue repair, embryogenesis, blood clotting, and cell migration/adhesion. Accordingly, various studies directed at providing a favorable cellular environment to promote cell proliferation involve fibronectin or particular fibronectin peptides. Many of those studies employ the Arg-Gly-Asp or RGD sequence, which is part of the cell binding domain of fibronectin (see, e.g., U.S. Pat. No. 5,677,276 (Dickerson et al.), and S. L. Schor et al., *J Cell Sci* 109:2581–2590 (1996)).

Recently, it has been reported that the isoleucine-glycine-aspartic acid (Ile-Gly-Asp or IGD) tripeptide sequence, a component of the fibronectin type I module, can induce cell migration of dermal fibroblasts (S. L. Schor et al., *J. Cell Sci* 112:3879–3888 (1999)). Biological activity has not previously been ascribed to the conserved IGD motif in fibronectin, although previous studies have implicated the ninth type I repeat, which contains the IGDS sequence, in the assembly of an extracellular fibronectin matrix (MA Chernousov et al., *J Biol Chem* 266:10851–10858 (1991)). In PCT Published Application No. WO 99/02674 (Schor et al./University of Dundee), certain IGD-containing peptides were described and the IGDS peptide was shown to increase fibroblast migration and vessel number under certain conditions in a rat wound healing model.

While significant advancements have been made in identifying and understanding various modulators of cellular migration and angiogenesis, there remains a pressing need for effective means to promote angiogenesis at ischemic sites in the body, such as the heart and tissues fed by the peripheral vascular system, to restore circulation to blood deprived organs and tissues affected by atherosclerotic disease.

SUMMARY OF THE INVENTION

The present invention seeks to provides compositions, devices and methods for use in growing new blood vessels to restore or improve blood flow to ischemic tissues of the body, especially for treating cardiac and peripheral blood vessel disease.

In one embodiment of the present invention, compositions are provided for promoting angiogenesis in a region of the body for which angiogenesis is desired, such as an area in need of angiogenesis (e.g., an an ischemic region). In a particular embodiment, a composition is provided comprising a protein having angiogenic activity and comprising a domain having the amino acid sequence isoleucine-glycine-aspartic acid ("IGD" in standard amino acid letter designation). In preferred embodiments, the complete amino acid sequence of the protein comprises fifty (50) or few amino acid residues, more preferably twenty-five (25) or fewer, more preferably still ten (10) or fewer.

In another embodiment, a composition is provided comprising a protein having angiogenic activity and the amino acid sequence of isoleucine-glycine-aspartic acid [SEQ ID NO: 1]. In yet another embodiment, a composition comprising a protein having angiogenic activity and the amino acid sequence glycine-glycine-isoleucine-glycine-aspartic acid-glycine-glycine [SEQ ID NO: 2] ("GGIDGGG") is provided. In a further embodiment, a composition comprising a protein having angiogenic activity and the amino acid sequence isoleucine-glycine-aspartic acid-isoleucine-glycine-aspartic acid [SEQ ID NO: 3] ("IGDIGD") is provided. In a still further embodiment, a composition comprising a cyclic protein having angiogenic activity and the amino acid sequence isoleucine-glycine-aspartic acid-isoleucine-glycine-aspartic acid [SEQ ID NO: 4] ("cyclic IGDIGD"). In a yet further embodiment, a composition is provided comprising a protein having angiogenic activity and an amino acid sequence designated by the formula:

ZZIGDZZ (FORMULA 1)

wherein I represents isoleucine, G represents glycine, D represents aspartic acid, and Z represents any of the twenty biological amino acids. The peptides of SEQ ID NOS: 1–4, and other representative IGD peptides have been surprisingly found to exhibit excellent biological activity, as assessed by their ability to induce migration in a variety of cell types, including human endothelial cells, human fibroblast cells and sheep nucleus cells.

In another embodiment, a composition comprising a protein having angiogenic activity and the amino acid sequence isoleucine-glycine-aspartic acid-serine [SEQ ID NO: 5] ("IGDS") is provided. In another embodiment, a composition comprising a protein having angiogenic activity and the amino acid sequence isoleucine-glycine-aspartic acid-glutamine [SEQ ID NO: 6] ("IGDQ").

In another embodiment of the present invention there is provided an angiogenic composition (i.e., a composition that exhibits angiogenic activity) comprising at least one of the peptides of SEQ ID NOS: 1–6 and Formula 1, and at least one angiogenic growth factor other than the foregoing peptide(s). In certain embodiments the other angiogenic growth factor is a bone-derived angiogenic protein mixture (BDAP), one or more bone morphogenetic proteins (BMPs), vascular endothelial cell growth factor (VEGF), basic fibroblast growth factor (bFGF), angiogenin, endothelial growth factor (EGF), platelet derived growth factor (PDGF), transforming growth factor-alpha (TGF-α), transforming growth factor-beta (TGF-β), or a tumor necrosis factor-alpha (TNF-α).

According to still another embodiment of the present invention, an angiogenic composition is provided that comprises at least one of the peptides if SEQ ID NOS: 1–6 and Formula 1, and at least one recombinant angiogenic growth factor.

In a further embodiment of the present invention, a composition is provided that is active for promoting cell migration and/or angiogenesis under cell growth promoting conditions. The composition comprises at least one of the peptides of SEQ ID NOS 1–6 and Formula 1, and a matrix material. In some embodiments, the composition also includes a pharmacologically acceptable carrier, and the composition may be sterilized for use in the body.

In certain other embodiments of the present invention, a method of promoting myocardial angiogenesis is provided. The method includes administering intramyocardially to an ischemic area of the heart of an individual in need of such treatment, a composition comprising at least one of the peptides of SEQ ID NOS: 1–6 and Formula 1 in a physiologically acceptable carrier, in an amount effective to enhance vascular endothelial cell migration and/or proliferation in the ischemic area.

In another embodiment of the method, the composition that is administered to the patient comprises, in addition to at least one of the above-identified peptides of SEQ ID NOS: 1–6 and Formula 1, a physiologically acceptable carrier, and at least one of the following growth factors: BDAP, one or more BMPs, VEGF, bFGF, angiogenin, EGF, PDGF, TGF-α, TGF-β, and TNF-α. In some embodiments the carrier comprises polyvinylpyrrolidinone. In a preferred embodiment, the method includes delivering the composition to the ischemic area by injection.

In another embodiment of the present invention, a method of promoting peripheral angiogenesis is provided that comprises administering to an ischemic area of an organ or tissue fed by a peripheral vessel of an individual in need of treatment, a composition comprising at least one of the peptides of SEQ ID NOS: 1–6 and Formula 1 in a physiologically acceptable carrier, in an amount effective to enhance vascular endothelial cell migration and/or proliferation at the ischemic area. The composition may also comprise one or more of the following growth factors: BDAP, one or more BMPs, VEGF, bFGF, angiogenin, EGF, PDGF, TGF-α, TGF-β, and TNF-α. The physiologically acceptable carrier may comprise polyvinylpyrrolidinone, and the method may comprise administering the composition to the ischemic area by hypodermic injection.

In still another embodiment of the present invention, a method of enhancing blood flow to an ischemic tissue of the body in an individual in need of treatment is provided. The method comprises administering an angiogenic composition containing at least one of the peptides of SEQ ID NOS: 1–6 and Formula 1 in a physiologically acceptable carrier to a defined area of the ischemic tissue, in an amount effective to stimulate vascular endothelial cell migration and/or proliferation sufficient to restore or increase blood flow to the ischemic tissue. In some embodiments, the method comprises delivering the composition to a site adjacent a native blood vessel narrowed due to atherosclerotic disease. The method may comprise delivering the composition to a site adjacent a bypass graft. Some embodiments of the method comprise delivering an angiogenic composition that contains, in addition to at least one of the peptides of SEQ ID NOS: 1–6 and Formula 1 and a carrier, at least one of the above-identified growth factors. These and other embodiments, features and advantages of the present invention will become apparent with reference to the following description and drawings.

BRIEF DESCRIPTION OF THE DRAWINGS

FIGS. 1A and 1B illustrate tabulated results of a cell migration assay for selected IGD-motif tripeptides according to the protocol of Experiment 1.

FIG. 1C provides photographs showing the results of cell migration assays for IGD-motif tripeptides as tested in Experiment 1.

FIG. 3A shows tabulated results of a quail CAM assay for four IGD-motif tripeptides according to Experiment 3.

FIG. 3B provides photographs of quail CAM assay results for selected IGD-motif tripeptides tested in Experiment 3.

DETAILED DESCRIPTION OF PREFERRED EMBODIMENTS

Figure 2:
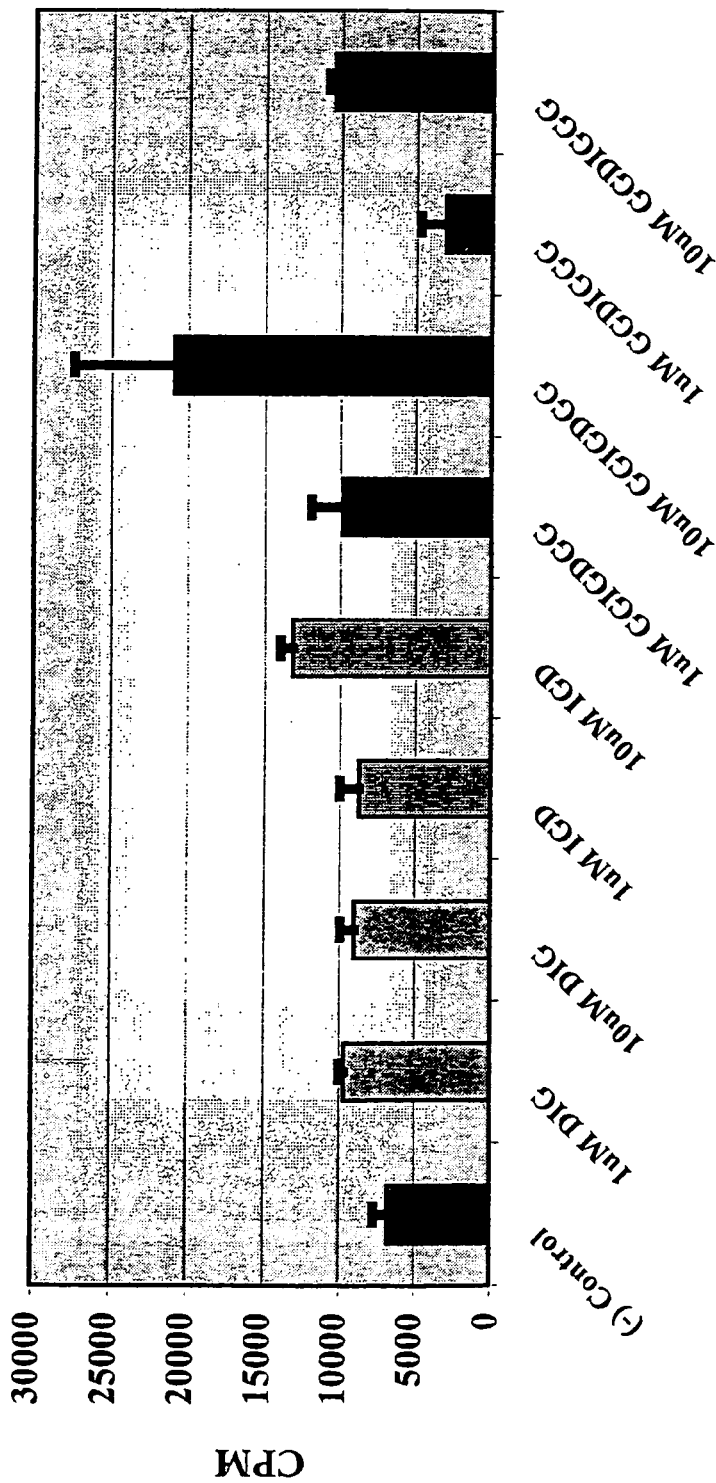
FIG. 2 shows tabulated results of a cell proliferation assay for four IGD-motif tripeptides according to the protocol of Experiment 2.

In the present disclosure, the terms "isoleucine-glycine-aspartic acid peptide," "Ile-Gly-Asp peptide," and "IGD containing peptide" all refer to a peptide having at least one isoleucine-glycine-aspartic acid sequence, and which has cell attachment promoting activity. "IGD" is the conventional amino acid code letter designation of that sequence. In its broadest sense, references to an IGD-motif peptide also include peptides that contain isoleucine-glycine-aspartic acid peptide or demonstrate cell attachment promoting properties similar to those of the isoleucine-glycine-aspartic acid sequence. Examples are Ile-Gly-Asp (IGD) [SEQ ID NO: 1]; Gly-Gly-Ile-Gly-Asp-Gly-Gly (GGIGDGG) [SEQ ID NO: 2]; Ile-Gly-Asp-Ile-Gly-Asp (IGDIGD) [SEQ ID NO: 3]; cyclic Ile-Gly-Asp-Ile-Gly-Asp (cyclic IGDIGD) [SEQ ID NO: 4]; Ile-Gly-Asp-Ser (IGDS) [SEQ ID NO: 5]; and Ile-Gly-Asp-Gln (IGDQ) [SEQ ID NO: 6]. The structures of these peptides are shown in the attached sequence listing. Other examples include peptides having an amino acid sequence characterized by Formula 1, or peptides of 50 or few amino acid residues and having a domain comprising the IGD sequence.

EXAMPLES

The peptides of SEQ ID NOS: 1–6 were synthetically made using a peptide synthesizer. Polyvinylpyrrolidinone (povidone) was obtained from IISP Chemicals (Wayne, N.J.). Human endothelial cells and human fibroblast cells were obtained from Clonetics (Walkersville, Md.).

Preparation of Sterile Formulations.

Sterile formulations of the IGD peptides as specified in SEQ ID NOS: 1–6 may prepared by synthesizing the peptides in a peptide synthesizer and filter sterilizing the resulting solutions using a 0.22 micron filter. The peptides can be lyophilized following the filter sterilization and reconstituted in 1% aqueous polyvinylpyrrolidinone or other povidone compounds as described in co-pending U.S. patent application Ser. No. 10/027,669, filed Dec. 21, 2001, entitled "POVIDONE-CONTAINING CARRIERS FOR POLYPEPTIDE GROWTH FACTORS," which is hereby incorporated herein in its entirety. Alternatively, other known carriers such as dilute HCl (10 mmol) may be used. Povidone is preferred as a carrier in conducting in vitro assays because it is not cytotoxic.

Example 1

In Vitro Cell Migration Assays

The ability of IGD-motif peptides according to the present invention to promote cell migration of human endothelial and smooth muscle cells, which are processes characteristic of angiogenesis, was evaluated by conducting cell migration assays for the peptides of IDG (SEQ ID NO: 1) and GGIGDGG (SEQ ID NO: 2), and a scramble of the IGD peptide characterized by the DIG sequence. A capped version of the scramble characterized by the GGDIGGG (SEQ ID NO: 7) sequence was also tested.

Chemotaxis trays (Chemo Tx disposable migration chamber, 6 mm diameter, 300 µl/well, 96 wells with 8 µm filter membranes from Neuro Probe, Inc., Gaithersville, Md.) for evaluating cell migration of the peptides were sterilized by placing the trays under UV light overnight. Further operations with the membrane were carried out under aseptic conditions. The filter membranes were loaded with gelatin to provide a suitable environment for the cells testing by soaking in 3% acetic acid overnight and then for 2 hours in 0.1 mg/ml gelatin. They were then rinsed in sterile water and allowed to air dry. Such membranes may be stored at room temperature for up to 1 month.

The cells to be used in the assay (endothelial cells or smooth muscle cells) were starved for 24 hours before use in appropriate culture media containing 0.1% Fetal Bovine Serum ("FBS") instead of the customary 10% FBS serum, and 1× penicillin-streptomycin antibiotics. The wells of the 96 well chamber of the chemotaxis unit were filled with media containing 0.1% serum alone or 0.1% serum and the test material (control or chemoattractant respectively). The filter membrane was positioned over the plate, aligning the holes in the corners of the frame with the four pins on the microplate, and the membrane was snapped into place making sure that the media in the wells touched the membrane completely. Fifty (50) µl of cell suspension in the starvation-media, at a concentration of $4 \times 10^4$ viable cells per charge were plated onto each site (over each well). The plate was incubated at 37° C. in an atmosphere of 5% $CO_2$ for 4 hours.

After incubation the lid was removed and with the filter still in place the cells on the upper surface of the membrane were gently wiped off and washed by carefully flushing the top surface of the filter with media by holding the plate with filter at a 45° angle over a container. The cells on the undersurface of the membrane were then fixed in methanol (~20 minutes) and stain with Diff-Quik Staining Set. The membrane was then allowed to dry and the number of cells that migrated through the filter pores was determined by counting the number in a field under a light microscope.

The results indicate that both the peptide of SEQ ID NO: 1 and SEQ ID NO: 2 promoted cell migration, for both the human aortic endothelial cells and the human smooth muscle cells. Neither the DIG scramble nor the capped GGDIGGG (SEQ ID NO: 7) scramble showed cell migration significantly greater than controls. See FIGS. 1A, 1B and 1C. A dose dependent effect was observed with the optimal concentration being 100 µM for the uncapped peptide. However, with the capped peptide better migration compared to the uncapped peptide was observed at a 10-fold lower concentration. The respective scramble peptides showed fewer cells migrating. FIG. 1C shows the migration of endothelial cells in a modified Boyden chamber assay in response to various treatments. Both IGD and GGIGDGG cause increased migratory response compared to either the negative control of the corresponding scramble peptides.

Example 2

In Vitro Cell Proliferation Assays

The capacity of IGD-motif peptides according to the present invention to promote cell migration of human aortic endothelial cells was evaluated by conducting in vitro cell proliferation assays for the peptide of IGD (SEQ ID NO: 1) and GGIDGG (SEQ ID NO: 2). the DIG scramble peptide, and the capped version of the scramble, GGDIGGG (SEQ ID NO: 7). Human aortic endothelial cells grown to ~95% confluency were seeded (5000 cells/well) in growth medium for four hours to allow cells to adhere. The cells were then transferred to the starvation medium described in Example 1 and starved for about 18 hours. The cells were then transferred to starvation medium containing the test peptide, and the cells were allowed to proliferate for an additional 48 hours. The medium was then removed and the wells were washed with PBS. The cells were then subjected to a single freeze-thaw cycle. CyQuant reagent (Molecular Probes, Eugene, Oreg.) was then added to the cells according to the manufacturer's instructions and the cells incubated for 5 minutes in the dark. The intensity of the color—which is directly proportional to the number of cells—is read at an excitation wavelength of 485 nm and the emission wavelength set at 535 nm.

The results indicate that both the peptide of SEQ ID NO: 1 and SEQ ID NO: 2 promoted cell proliferation of human aortic endothelial cells. Neither the DIG scramble nor the capped GGDIGGG scramble, in contrast, showed cell migration significantly greater than controls. See FIG. 2. It can be seen that with the capped tripeptide the proliferative response was nearly twice as great as that of the uncapped tripeptide. In either case the scramble peptides showed a significantly lower response than the active peptides.

Example 3

Quail Chorioallantoic Membrane (CAM) Angiogenesis Assay

The activity of IGD-motif peptides for inducing migration and proliferation in endothelial or smooth muscle cells in an in vitro quail chorioallantoic membrane (CAM) model was assayed in a similar manner to that described by Parsons-Wingerter et al., *Microvascular Research* 55:201–214 (1998), the disclosure of which is hereby incorporated herein by reference. Briefly, fertilized Japanese quail eggs (cotumix cotumix japonica) were opened onto petri dishes on day 3 post-incubation. After 7 days of culture, the four IGD-motif peptides tested in Examples 1 and 2 (IGD, GGIGDGG (SEQ ID NO: 2), DIG, GGDIGGG) each dissolved in in 1% polyvinyl pyrrolidine prewarmed to 37° C., were distributed evenly onto the surface of a CAM in separate petri dishes. After 24 hours of incubation, the CAM's were fixed, dissected and photographed at 10× magnification to visualize the arterial vascular tree, including end stage vessels. Digital images of triplicate CAM specimens were acquired at 10× magnification in grayscale, binarized to black-and-white, and skeletonized. The vessel branching pattern was analyzed and quantified by the fractal dimension.

The results indicate that both the IGD (SEQ ID NO: 1) and GGIGDGG (SEQ ID NO: 2) peptides promoted angiogenesis in the CAM model, while neither the DIG scramble nor the GGDIGGG (SEQ ID NO: 7) capped scramble promoted angiogenesis significantly better than controls. See FIGS. 3A and 3B. FIG. 3A shows data as a percent change over negative control, the negative being set at 100%. It can be seen that the capped peptide was better than the uncapped peptide at equivalent concentrations. As shown in FIG. 3B, the vessel density in 7 day old quail embryos treated with the capped IGD motif (GGIGDGG) resulted in increased vessel density compared to either the carrier alone (povidone) or the scramble peptide (GG-DIGGG) treatment.

The foregoing in vitro data strongly suggest that IGD-motif peptides will be angiogenic in known animal models involving, e.g., dogs or rabbits as well as in similar human clinical situations. An increase in blood vessel density, size and maturity of the vessels can be anticipated as outcomes of the studies in the animal models. The specificity to the peptide is clear, in view of the inability of the scrambled peptide to provoke a similar positive response in the in vitro studies.

In some instances, where either coronary or peripheral angiogenesis is desired, it may be preferable to also include a cell growth promoting matrix material with the IGD peptide injection composition in order to further enhance cell migration or recruitment and proliferation. Suitable matrix materials include polyvinylpyrrolidinone and dilute acidic solutions, e.g. 10 mmol HCl. The IGD peptide-matrix mixture is preferably introduced at the ischemic site where vascularization is desired.

Another alternative angiogenesis promoting compositions may comprise an IGD-motif peptide, such as any of the peptides of SEQ ID NOS: 1–6 or Formula 1, combined with a known angiogenic substance such as BDAP, one or more BMPs, VEGF, bFGF, angiogenin, EGF, PDGF, TGF-α, TGF-β, and TNF-αA preferred angiogenic composition comprises an IGD-motif peptide such as GGIGDGG and the bone-derived angiogenic protein mixture (BDAP) described in co-assigned U.S. Pat. No. 6,211,157. In another preferred embodiment, the composition comprises a mixture of at least one IGD-motif peptide of SEQ ID NOS: 1–6 and Formula 1 and VEGF. The resulting vascular endothelial cell migration stimulating effect and/or cell proliferation effect of the combination is expected to be additive or even synergistic compared to the effects of either the IGD peptide or the other growth factor alone. Either during embryologic development or during tissue regeneration in vivo, in non fetal tissues, several growth factors are upregulated—some simultaneously and others sequentially—indicating the involvement of more than one factor for the completion of the process. Some of the earlier clinical studies addressing the ability of single growth factors to induce angiogenesis have not been completely successful, further emphasizing the need for more than a single factor or signal transduction pathway.

In addition to the representative IGD-motif peptides discussed in the preceding examples, one could also or instead, under suitable circumstances, employ another cell migration stimulating IGD-motif peptide in the treatment methods described herein. Such IGD peptides are described in PCT Published Application No. WO 99/02674, which is hereby incorporated herein by reference.

While the preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. Accordingly, the scope of protection is not limited by the description or examples set out above, but is only limited by the claims which follow, that scope including all equivalents of the subject matter of the claims. Each and every claim is incorporated into the specification as an embodiment of the present invention. Thus the claims are a further description and are an addition to the preferred embodiments of the present invention.

The appended Sequence Listing is incorporated herein by reference.

---

What is claimed is:

1. The isolated peptide sequence GGIGDGG (SEQ ID NO: 2).

2. An angiogenic composition comprising the isolated peptide sequence GGIGDGG (SEQ ID NO: 2) and at least one angiogenic peptide selected from the group consisting of bone-derived angiogenic proteins (BDAPs), vascular endothelial cell growth factor (VEGF), basic fibroblast growth factor (bFGF), angiogenin, endothelial growth factor (EGF), platelet derived growth factor (PDGF), transforming growth factor-alpha (TGF-α), transforming growth factor-beta (TGF-β), and tumor necrosis factor-alpha (TNF-α).

3. The angiogenic composition of claim 2 wherein at least one said angiogenic peptide is a recombinant angiogenic peptide.

4. The angiogenic composition of claim 2 wherein said at least one angiogenic peptide is a bone-derived angiogenic protein (BDAP).

5. The angiogenic composition of claim 2 wherein said at least one angiogenic peptide is vascular endothelial cell growth factor (VEGF).

6. The composition of claim 2, further comprising a pharmacologically acceptable carrier.

7. The composition of claim 6 wherein the pharmacologically acceptable carrier comprises polyvinylpyrrolidinone.

8. The composition of claim 6 wherein the pharmacologically acceptable carrier comprises hydrochloric acid.

9. The composition of claim 6, wherein the composition further comprises polyvinylpyrrolidinone.

10. The composition of claim 6, wherein the composition further comprises hydrochloric acid.

11. The composition of claim 2, wherein the composition is an injectable solution.

12. A composition that is active for promoting cell migration and/or angiogenesis under cell growth promoting conditions, the composition comprising the isolated peptide sequence GGIGDGG (SEQ ID NO: 2) and a matrix material.

13. The composition of claim 12, further comprising a pharmacologically acceptable carrier.

14. The angiogenic composition of claim 12, further comprising at least one angiogenic peptide selected from the group consisting of bone-derived angiogenic proteins (BDAPs), vascular endothelial cell growth factor (VEGF), basic fibroblast growth factor (bFGF), angiogenin, endothelial growth factor (EGF), platelet derived growth factor (PDGF), transforming growth factor-alpha (TGF-α), transforming growth factor-beta (TGF-β), and tumor necrosis factor-alpha (TNF-α).

15. The angiogenic composition of claim 14 wherein said at least one angiogenic peptide is a bone-derived angiogenic protein (BDAP).

16. The angiogenic composition of claim 14 wherein said at least one angiogenic peptide is vascular endothelial cell growth factor (VEGF).

17. The composition of claim 12, further comprising a pharmacologically acceptable carrier.

18. The composition of claim 17 wherein the pharmacologically acceptable carrier comprises polyvinylpyrrolidinone.

19. The composition of claim 17 wherein the pharmacologically acceptable carrier comprises hydrochloric acid.

20. The composition of claim 12, wherein the composition is an injectable solution.

21. The composition of claim 20, wherein the composition further comprises polyvinylpyrrolidinone.

22. The composition of claim 20, wherein composition further comprises hydrochloric acid.

23. The angiogenic composition of claim 12 wherein said matrix comprises a cell growth promoting matrix.

* * * * *

SEQUENCE LISTING

```
<160> NUMBER OF SEQ ID NOS: 6

<210> SEQ ID NO 1
<211> LENGTH: 3
<212> TYPE: PRT
<213> ORGANISM: Artificial
<220> FEATURE:
<223> OTHER INFORMATION: SYNTHETIC PEPTIDE

<400> SEQUENCE: 1

Ile Gly Asp
1

<210> SEQ ID NO 2
<211> LENGTH: 7
<212> TYPE: PRT
<213> ORGANISM: Artificial
<220> FEATURE:
<223> OTHER INFORMATION: SYNTHETIC PEPTIDE

<400> SEQUENCE: 2

Gly Gly Ile Gly Asp Gly Gly
1               5

<210> SEQ ID NO 3
<211> LENGTH: 6
<212> TYPE: PRT
<213> ORGANISM: Artificial
<220> FEATURE:
<223> OTHER INFORMATION: SYNTHETIC PEPTIDE

<400> SEQUENCE: 3

Ile Gly Asp Ile Gly Asp
1               5

<210> SEQ ID NO 4
<211> LENGTH: 6
<212> TYPE: PRT
<213> ORGANISM: Artificial
<220> FEATURE:
<223> OTHER INFORMATION: SYNTHETIC PEPTIDE

<400> SEQUENCE: 4

Ile Gly Asp Ile Gly Asp
1               5

<210> SEQ ID NO 5
<211> LENGTH: 4
<212> TYPE: PRT
<213> ORGANISM: Artificial
<220> FEATURE:
<223> OTHER INFORMATION: SYNTHETIC PEPTIDE

<400> SEQUENCE: 5

Ile Gly Asp Ser
1
```

```
<210> SEQ ID NO 6
<211> LENGTH: 4
<212> TYPE: PRT
<213> ORGANISM: Artificial
<220> FEATURE:
<223> OTHER INFORMATION: SYNTHETIC PEPTIDE

<400> SEQUENCE: 6

Ile Gly Asp Gln
1
```